US008970829B2

(12) United States Patent
Caussin De Schneck et al.

(10) Patent No.: US 8,970,829 B2
(45) Date of Patent: Mar. 3, 2015

(54) FOULING DETECTION SETUP AND METHOD TO DETECT FOULING (75) Inventors: Claudia Caussin De Schneck, Düsseldorf (DE); Hartmut Forster, Meerbusch (DE); Karl Helminger, Ainring (DE); Ralf Krack, Schmallenberg (DE); Robert Najman, Konstancin-Jeziona (PL)

(73) Assignee: Ecolab USA Inc., St. Paul, MN (US)

( * ) Notice: Subject to any disclaimer, the term of this patent is extended or adjusted under 35 U.S.C. 154(b) by 229 days.

(21) Appl. No.: 13/513,261

(22) PCT Filed: Dec. 11, 2009

(86) PCT No.: PCT/EP2009/066923
§ 371 (c)(1),
(2), (4) Date: Sep. 10, 2012

(87) PCT Pub. No.: WO2011/069556
PCT Pub. Date: Jun. 16, 2011

(65) Prior Publication Data
US 2013/0003048 A1  Jan. 3, 2013

(51) Int. Cl.
G01N 21/59 (2006.01)
G01N 27/06 (2006.01)
(Continued)

(52) U.S. Cl.
CPC ............. *G01N 21/15* (2013.01); *B01D 65/10* (2013.01); *G01N 17/008* (2013.01); *G01N 2021/155* (2013.01); *G01N 2021/157* (2013.01)
USPC ............................. 356/72; 356/246; 356/432

(58) Field of Classification Search
CPC . B01D 65/10; G01N 21/15; G01N 2021/155; G01N 2021/157; G01N 17/008
USPC ................. 356/72, 432–444; 250/573–575; 210/739, 749, 96.1; 73/61.62, 861.95
See application file for complete search history.

(56) References Cited

U.S. PATENT DOCUMENTS 3,834,232 A * 9/1974 Gruner et al. .............. 73/861.12
4,766,553 A 8/1988 Kaya et al.
(Continued)

FOREIGN PATENT DOCUMENTS

EP 0531067 A1 3/1993
WO 2009066046 A1 5/2009
(Continued)

OTHER PUBLICATIONS

International Search Report from corresponding international application No. PCT/EP2009/066923, mailed Sep. 10, 2010, 3 pp.
(Continued)

*Primary Examiner* — Sang Nguyen
(74) *Attorney, Agent, or Firm* — Shumaker & Sieffert, P.A.

(57) ABSTRACT

The invention refers to a fouling detection setup (I) and method for determining the amount of fouling (5) of surfaces (3) of fluid (6) treating devices (2) and/or internal functional components (4) of such devices, which are exposed to said fluid and are subjected to fouling. Fouling detection setups and methods are useful for monitoring the amount of fouling of surfaces, e.g. heat-transfer surfaces and also for monitoring the cleaning procedure of such fluid treating devices and/or internal functional components of such devices. According to the invention the detection setup (I) comprises at least one first sensor (7), with means (9) for measuring the optical transparency T and/or electrical conductive conductivity Q of said fluid (6). The Sensor includes at least one sensitive area (8) that is located nearby and/or within said surfaces (3) and wherein said area is at least temporarily exposed to said fluid (6).

5 Claims, 4 Drawing Sheets (51) Int. Cl.
*G01N 21/15* (2006.01)
*B01D 65/10* (2006.01)
*G01N 17/00* (2006.01)

(56) References Cited

U.S. PATENT DOCUMENTS

| | | | | |
|---|---|---|---|---|
| 5,167,769 | A | * | 12/1992 | Jack et al. ................. 162/238 |
| 5,220,514 | A | * | 6/1993 | John .............................. 702/53 |
| 5,811,688 | A | * | 9/1998 | Marsh et al. ............. 73/861.25 |
| 5,992,505 | A | | 11/1999 | Moon |
| 6,023,070 | A | * | 2/2000 | Wetegrove et al. ........... 250/573 |
| 6,324,900 | B1 | | 12/2001 | Bruno et al. |
| 6,386,272 | B1 | * | 5/2002 | Starner et al. ............... 165/11.1 |
| 6,791,092 | B2 | * | 9/2004 | Hamilton ..................... 250/373 |
| 7,049,622 | B1 | * | 5/2006 | Weiss ........................... 250/577 |
| 7,270,015 | B1 | * | 9/2007 | Feller ......................... 73/861.95 |
| 2002/0108911 | A1 | * | 8/2002 | Xiong et al. ................. 210/739 |
| 2005/0000894 | A1 | | 1/2005 | Hedstrom et al. |
| 2005/0057753 | A1 | * | 3/2005 | Mosley et al. ............... 356/436 |
| 2006/0060787 | A1 | | 3/2006 | Herrington et al. |
| 2011/0286492 | A1 | * | 11/2011 | Auret et al. ..................... 374/1 |

FOREIGN PATENT DOCUMENTS

| | | |
|---|---|---|
| WO | 2011069556 A1 | 6/2011 |
| WO | 2012062372 A1 | 5/2012 |

OTHER PUBLICATIONS

Written Opinion of corresponding international application No. PCT/EP2009/066923, mailed Jan. 24, 2012, 6 pp.

International Preliminary Report on Patentability from corresponding international application No. PCT/EP2009/066923, dated Apr. 19, 2012, 14 pp.

Response to Written Opinion dated Jan. 24, 2012 for corresponding international application No. PCT/EP2009/066923, filed Mar. 12, 2012, 11 pp.

* cited by examiner

FOULING DETECTION SETUP AND METHOD TO DETECT FOULING

The invention refers to a fouling detection setup and a method for determining the amount of fouling of surfaces of fluid treating devices and/or internal functional components of such devices, which are exposed to said fluid and are subjected to fouling.

Fouling detection setups and methods are useful for monitoring the amount of fouling of surfaces of such fluid treating devices and/or internal functional components, e.g. heat-transfer surfaces and also for monitoring the cleaning procedure of such fluid treating devices and/or internal functional components of such devices which is commonly called CIP (Cleaning In Place).

A method and apparatus for testing the efficiency of a cleaning procedure for a filter in a filtering system is known from US 20050000894 A1. After the cleaning procedure, the system is pressurized and a decay in pressure over a predetermined time period is measured. Based on the pressure decay it is determined whether or not the cleaning procedure has been effective.

Such a system however, is incapable of determining the amount of fouling online. Other methods or setups exist, that are capable of measuring the amount of fouling online.

An apparatus for measuring a fouling resistance of the heat transfer from a heat-transfer surface and a cleanliness factor of a heat-transfer surface, which is capable of online monitoring a build up degree of deposits is known from U.S. Pat. No. 5,992,505A. The apparatus uses the given length of a given wire wound inside the heat-transfer surface for measuring an average temperature of the heat-transfer surface and an inlet/outlet portion water temperature measuring member for measuring the temperature of the inlet/outlet portions of the apparatus.

Another apparatus for online measuring the fouling of a fluid treating device including a heat exchanger is known from U.S. Pat. No. 4,766,553A. The apparatus calculates the heat-transfer coefficient as a function of the inlet/outlet temperatures, flow rate, area, and specific heat of the heat exchanger. The actual heat-transfer coefficient is compared with a nominal or original heat-transfer coefficient to determine if any deterioration in the coefficients has occurred which reflects the fouling of the heat exchanger.

However, a problem with known fouling detection devices is, that those devices can only detect fouling with respect to the operating parameters of the fluid treating device and/or internal functional components thereof itself, for example by measuring the internal pressure, heat transfer, or flow rate of the system. Hence, fouling detection occurs at a time, at which the operating parameters of the fluid treating device are already strongly deteriorated, which may lead to damage of functional components and may overrun the system. Furthermore, previously mentioned systems require multiple sensors, which increases the instability or failure of such systems.

The cleaning procedure is commonly performed by flushing the system with water with added detergents. Another problem that sometimes occurs is that the cleaning fails. In such case the following product cycle is shortened, which leads to product losses, since the system has to enter the cleaning phase sooner than calculated. Beforehand mentioned online monitoring systems are only designed for use with heat transfer surfaces or heat exchanger and can only measure the amount of fouling when the system is in operation, but not during the cleaning stage.

It is therefore an object of the present invention to provide a fouling detection device and/or method of the type described above, which avoids the aforementioned drawbacks.

This object is achieved by the fouling detection setup according to the present invention comprising at least one first sensor, which comprises means for measuring the electrical conductive conductivity and/or optical transparency of said fluid including at least one sensitive area that is located nearby or within said surfaces of the fluid treating devices and/or internal functional components of such devices, and wherein said area is at least temporarily exposed to the fluid.

A fouling detection setup according to the present invention can be used for fouling, scaling, and/or cleaning control of fluid treating devices that may include functional components, such as for example drain lines, UHT-(Ultra High Temperature) lines, pasteurizer lines, HTST-(High Temperature Short Time-) pasteurizer lines, cooling systems, and/or boiler systems.

With present invention, the operator of any fluid treating device can easily see when his installation needs to be cleaned and when each cleaning step can be ended. As a result, optimum runtimes are possible, which may lead to optimum process costs due to the easy to use and robust measuring system.

Another advantage of present invention is, that the measurement of only one parameter is sufficient for obtaining a measure for the amount of fouling of said exposed surfaces. Furthermore, the measurement is independent of any functional component, such that the measured parameter gives accurate results for fouling, even when fouling still might have only a minor effect on the operating parameters of the system.

According to the present invention, fluid treating devices may be tanks, pipes, containers, ducts, circulation systems, or any combination thereof. These fluid treating devices include one or more of internal functional components, which according to various embodiments of present invention may be heat-transfer surfaces, evaporators, homogenizers, mixing apparatus, mixing machines, or any combination thereof.

Said surfaces of said fluid treating devices and/or internal functional components thereof are exposed to said fluid and are subjected to fouling. They may include surfaces of internal functional components of such fluid treating devices. Said surfaces, that are under consideration, are subjected to fouling and may, therefore, be only temporarily exposed to the fluid, since after a certain amount of time, a layer of fouling may completely cover the respective surface.

According to the invention, said first sensor comprises an area that is located nearby or within said exposed surfaces. Therefore, similar to said exposed surfaces, said area of the sensor may be at least temporarily exposed to said fluid and is also subjected to fouling. Being located nearby or within said exposed surfaces, the amount of fouling of said area of the sensor represents the amount of fouling of said surfaces. According to the invention, said means for measuring the conductive conductivity and/or optical transparency preferably comprise said area.

According to the present invention every said first sensor, may comprise means for measuring a physical parameter, as for example the conductive conductivity and/or optical transparency. Said physical parameter should generally be independent of the amount of fouling of any surface of the fluid treating devices. However, according to the invention, said means for measuring said parameter are realized in such a way, that the measurement of the physical parameter with said means does show a strong dependence on the amount of fouling of these surfaces. The measurement of the physical parameter with measurement means according to present invention, results in a different value of the measured physical parameter, compared to the value of said physical parameter, that is obtained when the system is in its clean state. Accordingly any sensor, that may be used within a fouling detection setup according to the invention, may originally be designed to measure any arbitrary physical parameter, but when measuring said physical parameter, the value that is being delivered by said sensor strongly deteriorates in case of fouling of said sensor. Advantageously such a sensor comprises an area, that is subjected to fouling and wherein the fouling of said area is reason for said deterioration of said value. In this case, the area can be located nearby or within said exposed surfaces, that are under consideration, in order to have an accurate measure for the fouling of those exposed surfaces.

According to a preferred embodiment of the present invention any change in electrical conductive conductivity and/or optical transparency that is measured with said at least one first sensor, is a measure for the extend of fouling of said surfaces.

Further advantageous embodiments of the fouling detection setup and/or of the fouling detection method have been specified in the dependent claims and will be described in the following.

In a preferred embodiment of the fouling detection setup according to the invention, that comprises at least one sensor for measuring the electrical conductive conductivity of said fluid, the area of said measuring sensor may comprise at least one first electrically conductive surface, which may be used as a first electrode. The sensor may further comprise means for measuring the conductive conductivity between said first electrically conductive surface and a second electrically conductive surface, wherein this second conductive surface is at least temporarily exposed to said fluid. Said second electrically conductive surface may then be used as a second electrode.

Advantageously, the area of said sensor also comprises said second electrically conductive surface, however being located separate from said first electrically conductive surface. Other embodiments of the second electrically conductive surface are also possible according to the invention. Alternatively for example, the second electrically conductive surface may be embodied in any conductive component of the fluid treating devices, if there is any, or any other second electrically conductive surface external to said area of the measurement sensor, however being especially designed for usage as a second electrode of the measuring means.

According to the invention, said second electrically conductive surface may be less strongly subjected to fouling compared to the exposed surfaces, but it is also within the scope of the invention, if said second electrically conductive surface is not at all subjected to fouling, or is similarly subjected to fouling as said exposed surfaces. Any other geometry for measuring the conductive conductivity is generally possible, if only the measuring setup for measuring the conductive conductivity of the fluid shows a deterioration of the measurement result, that depends on the amount of fouling.

A possible embodiment of the electrical conductivity sensor, which may advantageously be implemented by a commercially available conductivity measuring cell, such as the LGP conductivity measuring cell "Pt100" of the company Ecolab Engineering. This specific electrical conductivity sensor is able to detect conductivity values in between 0 to 20 mS/cm and also includes a temperature measuring device. However, according to the invention, every other conductive conductivity sensor with at least one exposed measuring electrode, which according to the invention corresponds to the first electrically conductive surface included in the area of the measuring sensor, may be included in said means for measuring the conductive conductivity of the fluid. Advantageously such a sensor even has a larger detection range for conductivities in between 0 to 100 mS/cm for example.

Depending on the range of application of the fouling detection setup, the sensor for measuring the conductive conductivity may be specified accordingly. In one preferred embodiment of the invention, the fouling detection setup can be used to detect the amount of fouling of surfaces of fluid treating devices and/or internal function components of such devices, wherein in consecutive product cycles the fluid treating device may be used for different fluids. In such a case the intrinsic conductivity of the fluid, which generally can be measured with the fouling detection setup when the fluid treating device is in its clean state, may be different for every other fluid. In an embodiment of the present invention, which is suited for such a case, the fouling detection setup may comprise different conductivity measuring sensors, wherein every sensor may have a different measurement range and possibly also a varying accuracy. The fouling detection setup according to such an embodiment of the invention comprises means to detect whether the measured conductivity is within the range of values, for which the sensor is specified for and means to choose in between various sensors.

In a different embodiment of the present invention, the fouling detection setup comprises at least one sensor for measuring the optical transparency of the fluid, said area of said measuring sensor may comprise at least one optically transparent window. Since the area of the sensor is located nearby or within said exposed surfaces, said window may be also subjected to fouling. The sensor may further comprise means for measuring the optical transparency and/or the amount of scattering of the light that may be emitted into said fluid. For such reasons those means may comprise at least one light source and an optical detector, wherein said light source may emit light through said transparent window into said fluid and the optical detector may detect light which is scattered into said detector because of scattering effects within said fluid and possibly also within the fouling of said exposed surfaces. Various alternatives for positioning the optical detector are possible. In a preferred embodiment the optical detector is mounted right next to the light emitting device, whereas within another embodiment the detector is mounted spatially separated from the light detection device, behind a second transparent window. According to the invention said measurement window of the sensor may be subjected to fouling, which as a result decreases the transparency of said optical window.

A possible embodiment of the light emitting device is for example a laser, a light bulb, or a light emitting diode (LED). The preferred center wavelength for the light emitting device is in the range of the optical spectrum in which the fluid is generally transparent, but wherein any fouling is semi-transparent and/or absorbing. A possible implementation such a sensor for measuring the optical transparency of the fluid is realized by usage of a commercially available light detecting and/or light absorbing sensor, such as the near infrared absorption sensor HS 16-N manufactured by Optec. Furthermore, the fouling detection setup according to such an embodiment may include light reflecting means, such as for example mirrors.

The fouling detection setup in another preferred embodiment may further comprise a second sensor, which is located at a position, where the measured signal of the physical parameter does not deteriorate over time or may deteriorate over time much slower than the measured signal of the first sensor does. Said second sensor may comprise means for measuring the optical transparency and/or electrical conductivity of said fluid including at least one sensitive area, that is at least temporarily subjected to the fluid and that is positioned such, that it is either not subjected to fouling or is only subjected to fouling with an amount that is less than the fouling of said exposed surfaces of said fluid treating devices and/or internal functional components thereof. In a preferred embodiment of the fouling detection setup the area of the second sensor is subjected to fouling that is less than half of the amount of the fouling of said exposed surfaces of said fluid treating devices and/or internal functional components thereof.

In another embodiment of the fouling detection setup according to the invention, the fouling detection setup further comprises multiple of said first and/or second sensors and may also include means for calculating an average value of the measured values of multiple sensors. Alternatively or additionally, the fouling detection setup may comprise means for choosing one or the other signal of multiple of said first and/or second sensors for further processing, depending on the specifications of those sensors and/or deviating measurement values, which might indicate failure of the respective sensor.

In various different alternatives of the fouling detection setup, the fouling detection setup may further comprise at least one out of the following devices: a temperature measuring device, an inductive conductivity measuring device, a computation device, a data storage device, a visualization device, and/or any other output generating device, e.g. a display, data interface, and/or some analog signal.

A temperature measuring device may be used for normalizing the measured electric conductivity and/or transparency with respect to temperature. In one preferred embodiment of the invention, the temperature measuring device is included within the sensor for measuring the electric conductivity and/or transparency of the fluid. In another embodiment, the temperature measuring device is located such, that the temperature of the fluid at the position of the first and/or second sensor is determined indirectly, possibly by calculating means that use some implemented predefined temperature gradient for calculating the temperature at the respective location.

In a different embodiment of the invention the fouling detection setup may further comprise an inductive conductivity measuring device for measuring the electrical conductivity without being affected by fouling of said exposed surfaces. When measuring the electrical conductivity with an inductive conductivity sensor, the measured value is generally independent of any fouling of the sensor and implemented in a fouling detection setup of present invention may serve as a reference value for the measured conductive conductivity. In one preferred embodiment of the invention the fouling detection setup comprises at least one of said first sensors and at least one inductive conductivity measuring device.

A fouling detection setup according to the invention may further comprise means for determining a fouling parameter S by calculating the difference of the value measured with the inductive conductivity measuring device and the value measured with the conductive conductivity measuring device. A fouling detection setup, that also comprises an inductive conductivity measuring device, may be especially advantageous for arranging the fouling detection setup locally at only one position within and/or nearby said exposed surfaces.

As already mentioned previously, the fouling detection setup may further comprise a computation device for calculating a fouling parameter S. In such a case, all sensors and/or measuring devices of the fouling detection setup may be connected to an analog/digital (A/D-) converter, which converts the analog signal of the sensors and/or measuring devices into a digital value. The digital signal may be further transferred to said computation device.

The fouling detection setup may further comprise a data storage device for saving the measured values of the sensors and/or measuring devices and/or for saving any calculated fouling parameter S. In another embodiment of the fouling detection setup, the fouling detection setup may further comprise a visualization device for visualizing the fouling parameter S and/or the measured data over time and/or for the output of automated recommendations preferably with regard to cleaning requirements of the fluid treating devices and/or internal functional components thereof.

In an embodiment of the fouling detection setup according to present invention, the computation device may further include routines for calculating a fouling parameter S and for analyzing said fouling parameter S according to the method that is specified in the claims and/or the following description. In a preferred embodiment of the fouling detection setup, as it was previously described, the features of said fouling detection setup may be specified in such a way, that they allow to accomplish said method.

To achieve the objects mentioned in the introduction, there is further provided a method for determining the amount of fouling of surfaces of fluid treating devices and/or internal functional components of such devices exposed to said fluid, wherein the method includes the steps of: measuring the electrical conductive conductivity Q and/or optical transparency T of said fluid at locations which are chosen such that they are nearby or within said exposed surfaces and wherein a change in electrical conductive conductivity and/or optical transparency represents a measure for the extend of fouling of said exposed surfaces, determining a fouling parameter S, and analysis of said fouling parameter S, preferably by comparison of said fouling parameter S with a predefined reference value, preferably a fluid dependent predefined reference value.

The measuring of the electrical conductive conductivity Q and/or optical transparency T of said fluid is preferably performed such, that the means for measuring the electrical conductive conductivity Q and/or optical transparency T continuously remain at said locations within at least one product cycle of the fluid treating devices. Such a product cycle is defined as the time period between two cleaning procedures of the fluid treating devices and/or internal function components thereof. As such, said means for measuring the electrical conductive conductivity and/or optical transparency are preferably as much exposed to the fluid, as said surfaces. Any change of the measured electrical conductive conductivity Q and/or optical transparency T within said product cycle represents a measure for the extend of fouling of said exposed surfaces according to the invention.

The step of determining a fouling parameter S can be performed in various ways. In one alternative of the method according to the invention, the fouling parameter S directly equals the measured value (Q,T), that was measured in the measuring step. Alternatively the measured value may be normalized with a predefined conversion coefficients C.

The step of determining a fouling parameter S may further include a step of calculating the difference and/or relative difference of the measured value (Q,T) and a pre-defined reference value, which preferably corresponds to the value of said physical parameter $(Q_0, T_0)$, which may be measured when the system is in its clean state. Accordingly, said reference value is generally fluid dependent. Said difference between the measured value and said reference value may then be interpreted as a measure for the amount of fouling of said surfaces and, therefore, may be considered as fouling parameter S. When the fouling parameter S is above some predefined threshold value ($Q_T$,$T_T$), which may dependent on the fluid and/or fluid treating device, the step of analyzing said fouling parameter may result in a corresponding cleaning advise.

In an alternative of the method according to the invention, the measuring step further includes measuring the electrical conductive conductivity Q' and/or optical transparency T' of said fluid at locations that are chosen because they are particularly unaffected by fouling. These locations may be remote to said exposed surfaces that are under consideration, preferably upstream with respect to any internal functional component of said fluid treating devices.

The measured signal (Q',T') obtained from said locations, that are unaffected by fouling, may be used as a continuous reference value in such a way, that the difference (Q–Q', T–T') and/or relative difference ((Q–Q')/Q, (T–T')/T) between the measured value at locations subjected to fouling (Q,T) and at locations that are particularly unaffected by fouling (Q',T') is used as a measure for the amount of fouling of the exposed surfaces. The step of determining a fouling parameter S may then further include the step of calculating said difference, in order to associate the corresponding result with the fouling parameter S. The advantage of such a method, which can be performed by utilizing a fouling detection setup that comprises at least one first sensor and at least a second sensor according to the invention, is given by the fact, that knowledge of a fluid dependent reference value, for example the electrical conductivity and/or optical transparency ($Q_0$,$T_0$) of the fluid itself, is generally not necessary for interpreting the measured values for the conductive conductivity and/or optical transparency of the fluid at locations that are subjected to fouling. Furthermore, no previously measured reference value may be required.

In another alternative of the method according to the invention, besides of measuring the electrically conductive conductivity at a location that is subjected to fouling, the method may further include a step of measuring the electrical inductive conductivity $Q_{ind}$ of said fluid. The location for measuring the electrical inductive conductivity is arbitrary, and may be performed at a position, that is close to said exposed surfaces, preferably at the same position where the conductive conductivity is being measured. The advantage of measuring the inductive conductivity $Q_{ind}$ is given by the fact, that generally its value is independent of the fouling of any of said exposed surfaces. The step of determining a fouling parameter S may further include the step of calculating the difference (Q–$Q_{ind}$) and/or relative difference (Q–$Q_{ind}$/Q) between the measured value Q that is obtained when measuring the conductive conductivity at a position that is subjected to fouling and when measuring the electrical inductive conductivity $Q_{ind}$.

Furthermore the measuring step may also include measuring the temperature of the fluid. Preferably the temperature is being measured at the same locations, where the conductivity (Q,Q', $Q_{ind}$) and/or optical transparency (T,T') of the fluid is being measured. The step of determining a fouling parameter S may then comprise a normalization of the measured conductivity (Q,Q', $Q_{ind}$) and/or optical transparency (T,T') with respect to temperature. This normalization can be performed according to a linear relationship between conductivity and/or optical transparency and temperature, or any other predefined functional relationship, which preferably is chosen with respect to the fluid.

In one preferred alternative of the method according to the invention, the steps of measuring, determining a fouling parameter, and analyzing said fouling parameter are performed simultaneously with any operation of the fluid treating devices and/or functional components thereof. Alternatively, the step of measuring and/or determining a fouling parameter is repeated for an arbitrary number of times before the remaining steps are performed. Preferably, all steps are done repeatedly after predefined time intervals Δt. According to this preferred alternative of the method, fouling of said exposed surfaces can be monitored online.

According to an alternative of the method, the step of determining the fouling parameter S may include calculating the fouling parameter S as a function of the measured values of the electrical conductivity (Q,Q', $Q_{ind}$) and/or optical transparency (T,T'). Preferably, this function is linear with respect to the measured values, however it may also be any kind of polynomial of order N with pre-defined conversion coefficients $C_i$. Preferably, these conversion coefficients $C_i$ are chosen according to the respective sensor that is being used within the measuring step. The conversion coefficients $C_i$ may be determined within some previously performed calibration step.

Within another alternative of the method, the step of determining said fouling parameter S further includes saving the fouling parameter S with respective data acquisition and/or data storage means and/or the step of analysing said fouling parameter S includes retrieving a set of previous fouling parameters from the data storage means and visualizing said set of fouling parameters. Analysing said fouling parameter may, however, be also realized by comparing the fouling parameter S with some predefined threshold value $S_T$. In case the fouling parameter S is larger than said threshold value $S_T$, the method may further include a step of notifying the user of the fluid treating devices and/or internal functions thereof.

According to a further alternative of the method according to the invention, the step of analyzing said fouling parameter S may also include calculating a second parameter S', which is a measure for the change over time of the fouling parameter S, preferably by numerically calculating the first derivative f'(S) of the fouling parameter S and comparing this second parameter S' with some other predefined threshold value $S'_T$. Preferably the step of analysing results in indicating the necessity for cleaning, when the magnitude of parameter S' is smaller than said predefined threshold value $S'_T$.

In an alternative of the method according to present invention, the fluid is a mixture containing a suspension and/or emulsion. Preferably the fluid is a mixture mostly containing milk. The fluid treating device with internal functional components may be for example an UHT line. High temperatures may cause a denaturation of the milk, which may be the cause for fouling of the surfaces of the UHT-line, that are downstream of the heat generating element. However, any other type of fluid may be treated within the fluid treating device and choosing any kind of preferred fluid does not restrict the present invention in any way.

A further alternative of present method may include a step of measuring the conductive conductivity and/or optical transparency at various locations within the fluid treating devices and/or functional components thereof and/or at different times, preferably integer fragments of said time interval Δt. An additional step of calculating an average value may increase the accuracy of the determination of the fouling parameter S.

In case of measuring the electrical conductive conductivity and/or optical transparency at more than one location, the determining step of the fouling parameter S may be performed by taking an average value.

Other objects, features and advantages of the present invention will appear from the following detailed disclosure of a preferred embodiment, from the enclosed patent claims as well as from the accompanying drawings.

BRIEF DESCRIPTION OF THE DRAWINGS

A preferred embodiment of the present invention will now be described in greater detail below with reference to the accompanying drawing, in which.

DETAILED DESCRIPTION OF A PREFERRED EMBODIMENT

Figure 1:
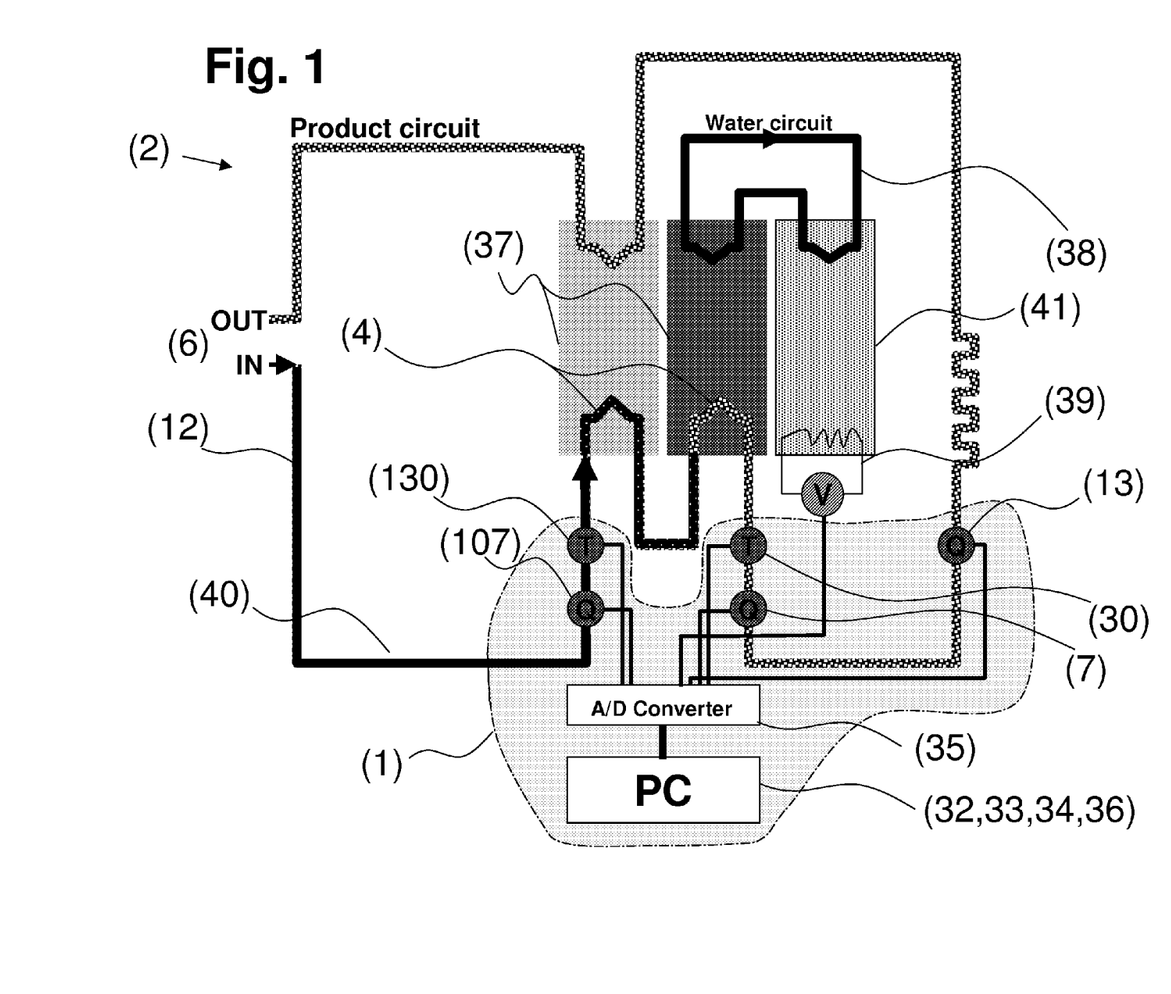
FIG. 1 is a schematic view of a fluid treating device with internal functional components, including a fouling detection setup according to the invention.

In FIG. 1, a fluid treating device (2) for pasteurizing a fluid, preferably some mixture containing milk, is shown schematically. The product circuit (12) of the fluid treating device (2) contains an UHT line, which comprises pipes and tanks and two heat exchangers (37) for heating the fluid (6), which according to the preceding description are representing said internal functional components of the fluid treating device (12). The product circuit (12) has an inlet portion for feeding the fluid (6) into the product circuit (12) and an outlet portion for withdrawal of fluid (6). The fluid first passes through a first heat exchanger (37), for preheating the fluid (6) by thermodynamic contact with those portions of the fluid (6) that have already passed most parts of the product circuit (12) and are just before exiting the product circuit (12) through the outlet portion. After being preheated in the first heat exchanger (37), the fluid is being guided through a pipe into a second heat exchanger (37), where it is being heated to high temperatures by thermodynamic contact with an external water circuit (38). The water in the external water circuit (38) has been heated by passage through a third heat exchanger (41), which is driven by steam and/or some electrically powered heat source (39). The heat source also includes an electrical output, which may serve as a measure for the temperature of the water circuit. After and/or while being heated in the first and second heat exchanger, the fluid (6) may cause fouling (5) on the surfaces (3) of the fluid heating device and the heat-exchangers, which are located right at the beginning of the first heat exchanger and downstream of that. Especially for milk, such fouling (5) is anticipated, since milk denaturizes at large temperatures, which causes said fouling (5). The fluid is further guided through pipes, possibly also including tanks for keeping the fluid above a certain temperature for a certain amount of time. Before leaving the product circuit (12) the fluid (6) preheats those portions of the fluid that enter the product circuit (12) through thermodynamic contact within a first heat exchanger (37), as already said before.

The fouling detection setup (1) according to the preferred embodiment of present invention as shown in FIG. 1 comprises two sensors (7,107) with means for measuring the conductive conductivity of the fluid (9, 109), two temperature measurement devices (3, 130), a sensor for measuring the inductive conductivity of the fluid (13), an analog digital converter (35), and a Personal Computer (PC) (36). The latter includes a computation device (32), a data device (33), and a visualization device (34).

Figure 2:
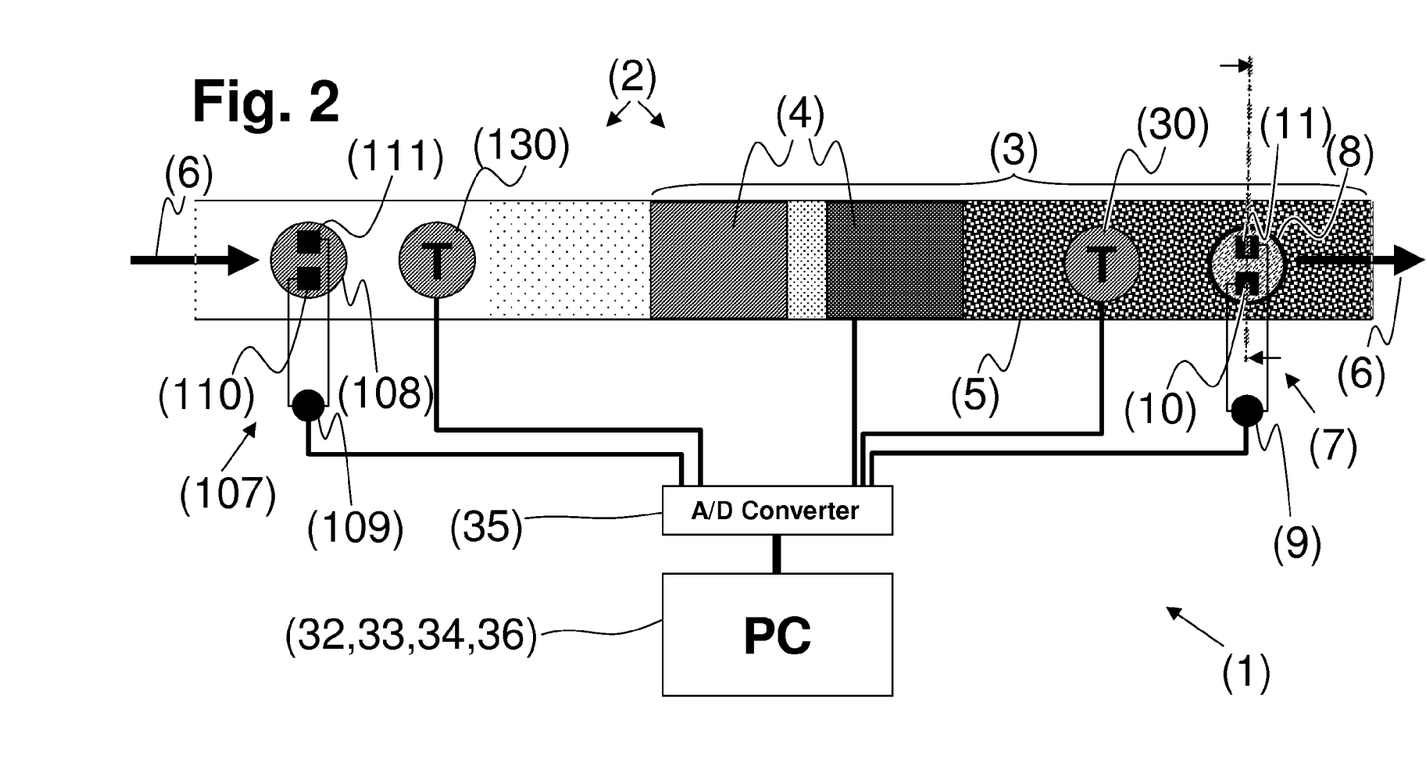
FIG. 2 is a schematic view of the surfaces of the fluid treating device and internal functional components thereof as they are arranged in the streaming direction of the fluid, including a fouling detection setup, according to the invention.

The first sensor (7) for measuring the conductive conductivity of the fluid is positioned such, that the area (8) of the sensor, as can be seen in FIG. 2 is located within the exposed surfaces (3) of the fluid treating device and heat exchangers thereof, which are subjected to fouling (5). Therefore, said area (8) of the sensor (7) is also subjected to fouling (5), in such a way that the fouling (5) on this area (8) represents the fouling of the surfaces (3) of the fluid treating device, including those of the heat exchangers. One of the temperature measuring devices (30) is located nearby, in order to measure the temperature of the fluid at the position, where the electrical conductivity of the fluid (6) is being measured. The sensor for measuring the temperature (30) and the sensor (7) for measuring the conductive conductivity of the fluid are schematically shown in FIGS. 1 and 2 as being separate, however, in a preferred embodiment of the invention both devices can be combined in one single device.

The second temperature measuring device (130) and the sensor (7, 107) with means for measuring the conductive conductivity of the fluid (109) are positioned upstream within the fluid treating device with respect to the heat-transfer surfaces (4) within the first and second heat exchangers (37). At this position the fluid is not heated yet, and therefore does not generate any fouling on nearby surfaces of the fluid treating device. Within one product cycle, which preferably is the time period in between two cleaning processes, the measured conductive conductivity of the sensor (107), which is located upstream to the water chamber for heat transfer (37), generally should remain constant. On the other hand the measured conductive conductivity of the first sensor (7) changes, because of the fouling (5) of the surfaces (3) of the fluid treating device which are at and/or downstream the heat exchangers (37). The fouling (5) is generated due to the increased temperature of the fluid (6).

The fouling detection setup (1) further includes a sensor for measuring the inductive conductivity of the fluid (13). The position of the sensor (13) in this specific embodiment is located downstream the heat exchangers (37), but can be located at any position within the fluid treating device (2). The inductive conductivity of the fluid (6) should generally remain constant within one operating cycle, since the inductive conductivity of the fluid is measured such, that any fouling of surfaces within the fluid treating devices or of the sensor does not deteriorate the signal which is being measured.

All sensors are connected to an analog/digital-(A/D-)converter, which converts the measured values of the sensors into a digital signal. The digital signal is being transferred to a computation device, which according to the present embodiment of the invention is included in a personal computer (36). Any measured value can be visualized by using a visualization device (34), which is connected to the Personal Computer (36), which may also include any computed fouling parameter or any automated recommendations based on a comparison of the fouling parameter with predefined threshold values or reference values.

In FIG. 2 the fluid stream (6) is shown schematically as it passes along various components of the surfaces of the fluid treating device, including internal functional components thereof (3) and the fouling detection setup (1) according to a preferred embodiment of the invention, which is shown in FIG. 1. The functional components that are being passed include the heat transfer surfaces (4) of the first and second heat exchanger (37). According to the schematic view of FIG. 2 the fluid first passes the sensor with means for measuring the conductive conductivity of the fluid (109) and the temperature measuring device (130). At the position of those devices the fluid (6) is not yet heated and therefore does not generate any fouling (5) on the surfaces of the fluid treating device. Following the stream of the fluid (6) to the right, as it is shown in FIG. 2, the fluid (6) passes the surfaces of the heat exchangers (4, 37). The fluid (6) is thereby heated and may start to generate fouling (5) on the surfaces (3) of the fluid treating device and the heat exchangers. At the position where the surfaces (3) of the fluid treating device and those of the heat exchangers are being subjected to fouling (5) an additional temperature sensor (30) and a sensor (7) for measuring the conductive conductivity of the fluid has been arranged.

Both sensors (7, 107) for measuring the conductive conductivity of the fluid are schematically shown in FIG. 2 by comprising an area (8, 108) that is located within the respective surfaces of the fluid treating device (2) and may be subjected to fouling, as it is the case for the sensor (7) downstream of the heat exchangers (4, 37). The sensor (7) further comprises means to measure the electrical conductive conductivity (9, 109) of the fluid, wherein these means are connected to a first electrically conductive surface (10, 110) and to a second electrically conductive surface (11, 111), wherein in this specific embodiment of the invention both conductive surfaces (10, 110, 11, 111) are located within said area (8, 108) of the sensor (7, 107). The conductive surfaces of the sensor (10, 110, 11, 111) are therefore similarly subjected to fouling as the area (8, 108) of the sensor (7, 107). Once again the sensors are connected to an analog digital converter (35) which is connected to a Personal Computer (36), including a computation device (32), a data device (33), and a visualization device (34).

Figure 3:
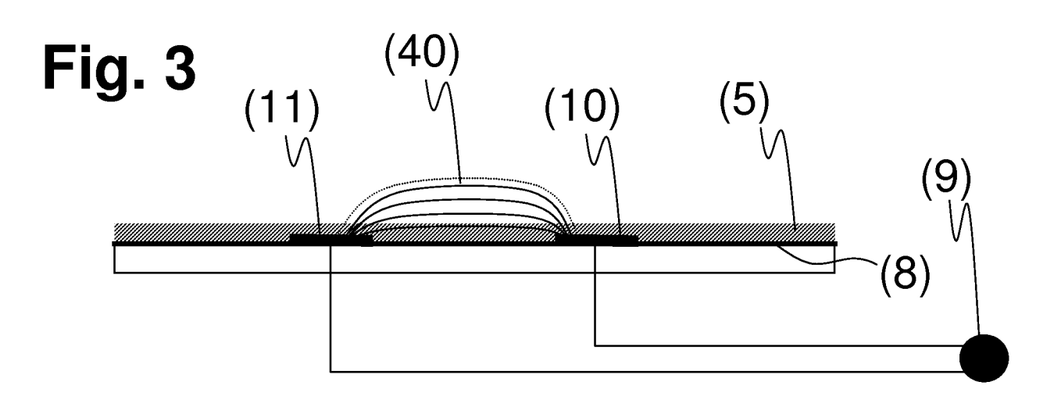
FIG. 3 is a schematic view of a sensor along the cutting line in FIG. 2.

FIG. 3 shows a schematic view of the sensor (7) for measuring the conductive conductivity of the fluid along the cutting line in FIG. 2. The Figure shows the area (8) of the sensor which is being subjected to fouling (5) and which includes a first electrically conductive surface (10) and a second electrically conductive surface (11). Both are connected to means for measuring the electrical conductive conductivity (9). Furthermore, FIG. 3 shows the course of field lines (40) in between the first (10) and second electrically conductive surface (11). Depending on the amount of fouling (5) the electrical field lines (40) partially pass through a layer of fouling (5) and the fluid itself.

Figure 4:
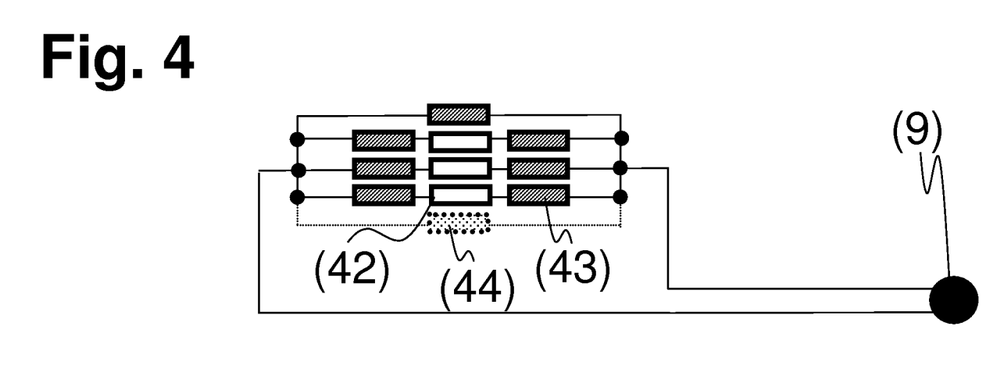
FIG. 4 is an equivalent circuit diagram for the sensor shown in FIG. 3.

In FIG. 4 an equivalence circuit diagram is shown for the electrical current in between the first and second conductive surface for every electrical field line (40), which are represented in FIG. 3. An equivalent electrical resistance (44) for all remaining field lines is shown schematically. As can be seen, the electrical resistance for every path of current along any one of the field lines can be considered as a series connection of an electrical resistance that depends on the amount of fouling (43) and another resistance (42), representing the electrical resistance of the fluid (6). Within one product cycle, the equivalent electrical resistance (43) of the fouling layer (5) increases, caused by the increasing thickness of the fouling layer (5).

Figure 5:
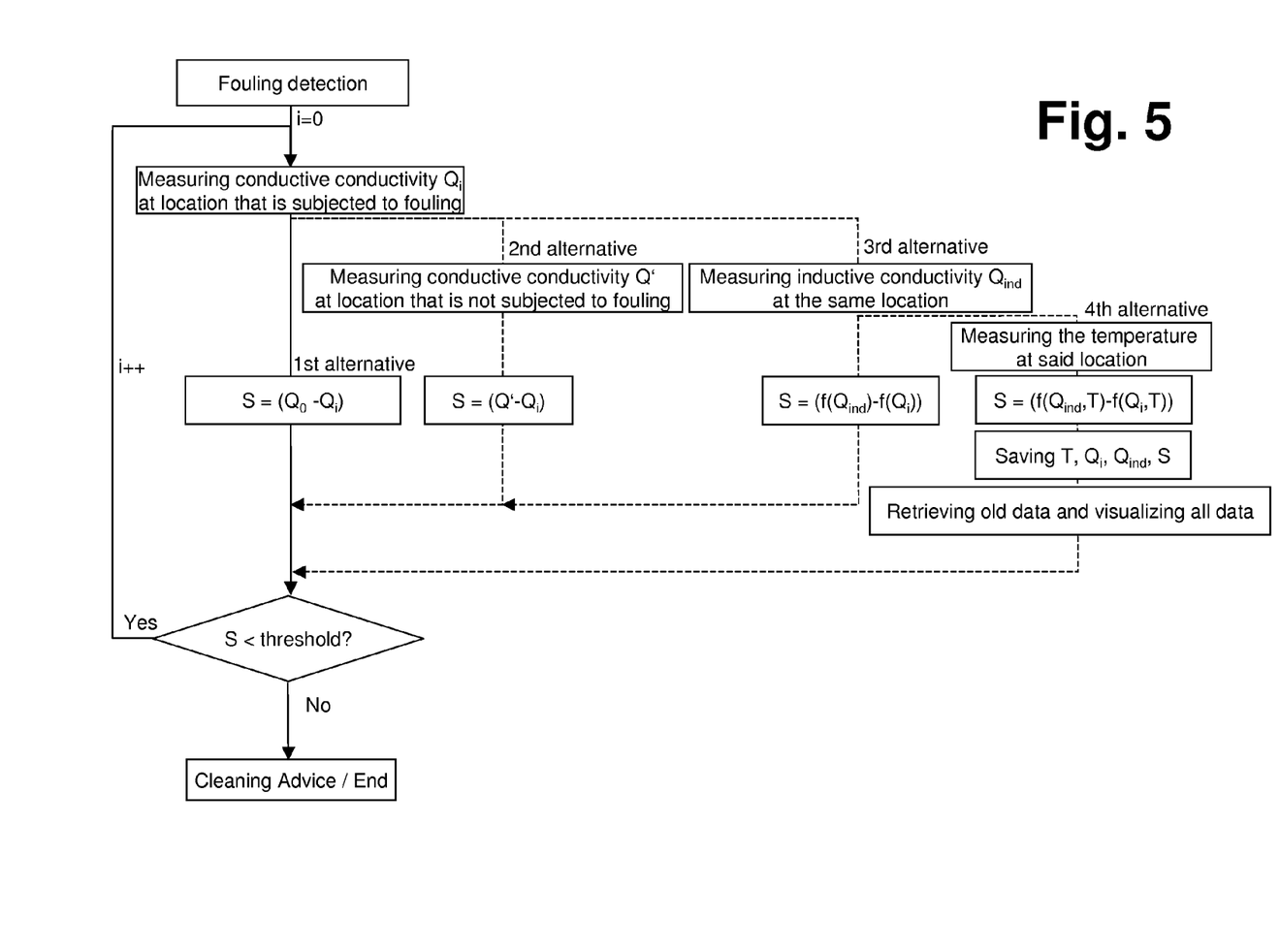
FIG. 5 is a flow chart of four various alternatives of the method according to the invention.

In FIG. 5 a flow chart of four various alternatives of the method according to this invention is shown. The flow chart graphically demonstrates the steps of the fouling detection method while using the fouling detection setup according to the embodiment, that has been described before. All alternatives, which are shown in FIG. 5, start with a measuring step, which includes measuring the electrical conductive conductivity $Q_i$ at a location that is subjected to fouling. With respect to the fouling detection setup according to FIG. 1, the measuring step can be performed by utilizing the electrical conductive conductivity sensor (7), which is located downstream of the surfaces of the heat exchangers (37,4).

In one possible alternative of the method according to the invention, the step of determining a fouling parameter S is realized according to the first alternative, shown in FIG. 5 on the very left side. In this case, the fouling parameter S is being calculated as the difference between the measured conductive conductivity $Q_i$ and a predefined reference value, which according to this alternative is given by the measured conductive conductivity at the beginning of the measurement cycle. Preferably, the measurement cycle starts at the same time as the product cycle. In that case, the conductive conductivity $Q_0$ is measured in the clean stage of the fluid treatment device and should therefore correspond to the physically anticipated, fluid dependent electrical conductivity of the fluid. The step of analyzing includes checking, if the saturation parameters exceeds a threshold value, which in the affirmative case causes a step of issuing a cleaning advice. The step of measuring, determining and analyzing is being repeated continuously, preferably starting at predefined time intervals $\Delta t$. The index i represents an increasing integer number, which continuously increases with every new measurement step.

Within a second alternative of the method, the step of measuring further includes measuring the conductive conductivity Q' at a location that is not subjected to fouling. When considering the fluid treating device and/or internal functional components thereof according to FIG. 1, the step of measuring the conductive conductivity Q' can be performed by utilizing the sensor (107) of the fouling detection setup, which is located upstream of any internal functional components. In this case the step of determining a fouling parameter S is performed by calculating the difference between the conductive conductivity Q', which was measured at a location that is not subjected to fouling and the conductive conductivity Q, which was measured at a location that is subjected to fouling. The step of analyzing remains equal to the alternative described before.

The third alternative of the method, which is schematically shown in FIG. 5 is performed such, that the measurement step includes measuring the inductive conductivity $Q_{ind}$. Since the inductive conductivity is independent of the amount of fouling of any surface within the fluid treating device and/or internal functional components thereof, the advantage of this method is given by the fact, that the measurement of the inductive conductivity can be performed at the same position in which the conductive conductivity was measured. According to the $3^{rd}$ alternative of the method, as it is shown in FIG. 5, the step of determining a fouling parameter includes calculating the saturation parameter as the difference between a function of the inductive conductivity and a function of the conductive conductivity. These functions might be any kind of polynomial and are specified according to the sensor that was used for measuring the respective value. The polynomial might have been pre-determined specifically for each sensor within a previous calibration step, which is not shown in FIG. 5. However, the saturation parameter S might as well be calculated by directly calculating the difference between the measured inductive and conductive conductivity. Once again the step of analyzing said fouling parameter S remains the same.

Within a 4$^{th}$ alternative of the fouling detection method, as it is shown in FIG. 5, the step of measuring further includes measuring the temperature of the fluid at the position in which the inductive conductive and/or the conductive conductivity was measured. The step of determining a fouling parameter now includes the step of normalizing the measured conductivity with respect to temperature. Hence, in FIG. 5, the step of calculating the fouling parameter includes respective functions which also depend on the temperature T next to the measured conductivity Q or Qind.

The 4$^{th}$ alternative, as it is shown in FIG. 5, further includes the step of saving all measured values and another step of retrieving old data values, which are being visualized with respective visualizing means.

The method according to the invention also includes any other alternative, which might be a combination of those previously described alternatives or any other which is in accordance with the features of the claims.

The invention has been described above mainly with reference to a preferred embodiment of the fouling detection setup (1). However, other embodiments than the one disclosed above are also possible within the scope of the invention, as defined by the appended patent claims.

1 Fouling detection setup
2 Fluid treating devices
3 Exposed surfaces of fluid treating devices and heat exchangers that are subjected to fouling
4 Heat transfer surfaces
5 Fouling
6 Fluid
7, 107 Sensor
8, 108 Area/Area of sensor
9, 109 Means to measure electrical conductive conductivity of the fluid
10, 110 First electrically conductive surface
11, 111 Second electrically conductive surface
12 Product circuit, including pipes and tanks
13 Inductive conductivity sensor
30, 130 Temperature measuring device
31 Inductive conductivity measuring device
32 Computation device
33 Data device
34 Visualization device
35 A/D Converter
36 PC
37 Heat exchanger for heat transfer
38 Water circuit for heat transfer
39 Heat generating element, including electrical supply and output for
40 Electrical field line
41 Heat exchanger for heat transfer
42 Equivalent electrical resistor for current through any fluid
43 Equivalent electrical resistor for current through any fouling
44 Equivalent electrical resistor

The invention claimed is:

1. A fouling detection setup for determining the amount of fouling of surfaces of fluid treating devices and/or internal functional components of such devices, wherein the surfaces are exposed to a fluid and subjected to fouling, comprising:
at least one first sensor that measures an optical transparency, T, of the fluid at at least one sensitive area associated with the surfaces that are at least temporarily exposed to the fluid; and
a second sensor that measures an optical transparency, T', of the fluid at an area that is not subjected to fouling;
a computation device that determines a fouling parameter, S, based on the measured optical transparency, T, of the fluid at the at least one sensitive area associated with the surfaces that are at least temporarily exposed to the fluid and the measured optical transparency, T', at the area that is not subjected to fouling;
wherein the computation device further automatically generates cleaning advice based on the fouling parameter, S; and
a visualizing device that displays at least one of the fouling parameter, S, the measured optical transparency over time, and the cleaning advice.

2. The fouling detection setup according to claim 1, wherein the detection setup comprises a further pair of first sensor and second sensor, wherein first sensor of the further sensor pair measures an electrical conductive conductivity, Q, of the fluid at least one sensitive area associated with the surfaces and wherein the area is at least temporarily exposed to the fluid, and wherein the second sensor of the further sensor pair measures the electrical conductivity, Q, of the fluid at an area that is not subjected to fouling.

3. The fouling detection setup according to claim 1, wherein the area of the measuring sensor, comprises at least one first electrically conductive surface and the sensor further comprises a second electrically conductive surface, which is at least temporarily exposed to the fluid.

4. The fouling detection setup according to claim 1, wherein the area of the measuring sensor, comprises at least one optically transparent window and the means for measuring the optical transparency comprise a light source and an optical detector, wherein the light source emits light through the transparent window into the fluid and the optical detector detects light which is scattered into the detector from the fluid.

5. The fouling detection setup according to claim 1, further comprising:
a temperature measuring device that normalizes the measured optical transparency, T, with respect to temperature; and
an inductive conductivity measuring device that measures the electrical conductivity of the fluid without being affected by fouling of said surfaces.

* * * * *